United States Patent [19]

Weiss

[11] 4,104,530

[45] Aug. 1, 1978

[54] DENTAL AND MEDICAL X-RAY APPARATUS

[75] Inventor: Mortimer E. Weiss, Laguna Beach, Calif.

[73] Assignee: Thoro-Ray Inc., Santa Ana, Calif.

[21] Appl. No.: 728,959

[22] Filed: Oct. 4, 1976

Related U.S. Application Data

[63] Continuation-in-part of Ser. No. 672,608, Apr. 1, 1976, abandoned.

[51] Int. Cl.² .................. H01J 35/00; H05G 1/00
[52] U.S. Cl. ................... 250/490; 250/439 P; 250/515
[58] Field of Search .............. 250/404, 439 P, 510, 250/399, 490, 505, 515

[56] References Cited

U.S. PATENT DOCUMENTS

| 1,881,448 | 10/1932 | Forde et al. | 250/399 |
| 2,531,583 | 11/1950 | Ott | 250/404 |
| 2,946,892 | 7/1960 | Bas-Taymaz | 250/404 |
| 3,906,235 | 9/1975 | Fischer | 250/404 |

Primary Examiner—Alfred E. Smith
Assistant Examiner—B. C. Anderson
Attorney, Agent, or Firm—William W. Haefliger

[57] ABSTRACT

Dental X-ray apparatus characterized by very substantial reductions in radiation exposure of the patient, comprises:

(a) X-ray tube means providing an electron beam,
(b) a beam target carried by said means and located axially rearwardly thereof to be received rearwardly into a patient's mouth,
(c) the target angled relative to said axis to produce a radiation pattern that extends forwardly of the target and also rearwardly and sidewardly of the target, and
(d) a shield adjacent the target rearwardly thereof and extending forwardly above and below the target. The shield may also define a tongue suppressor and may be removably mounted on the tubular carrier for the target. An extra-oral adapter is also provided, to removably fit on the carrier tube. Structure carried by the tube means projects an image delineating the main path of the X-ray beam.

21 Claims, 18 Drawing Figures

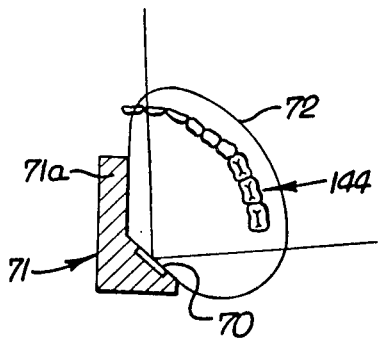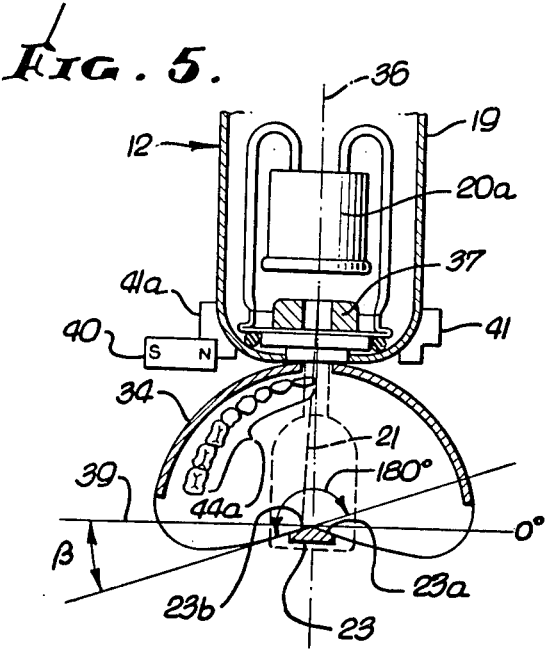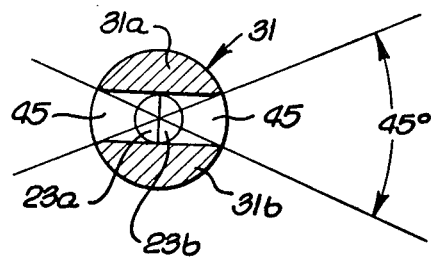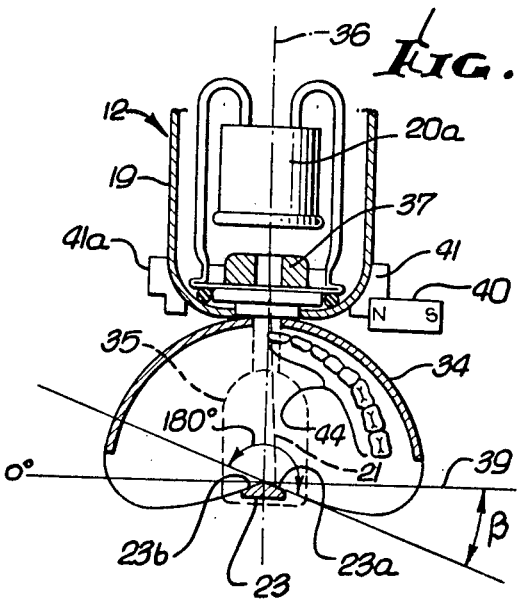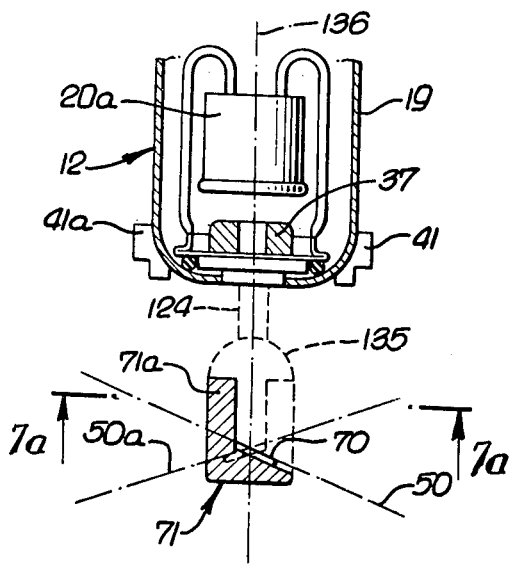

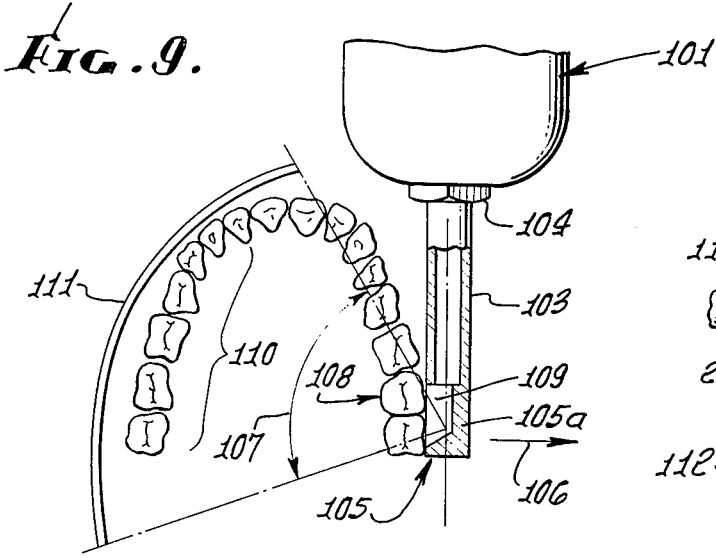
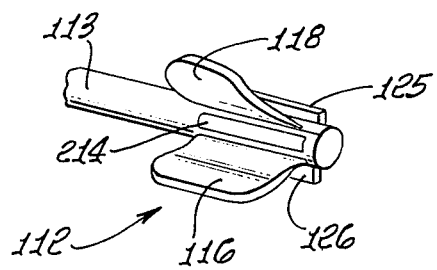
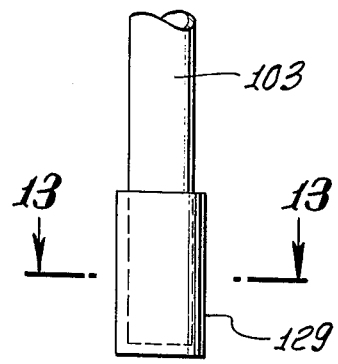
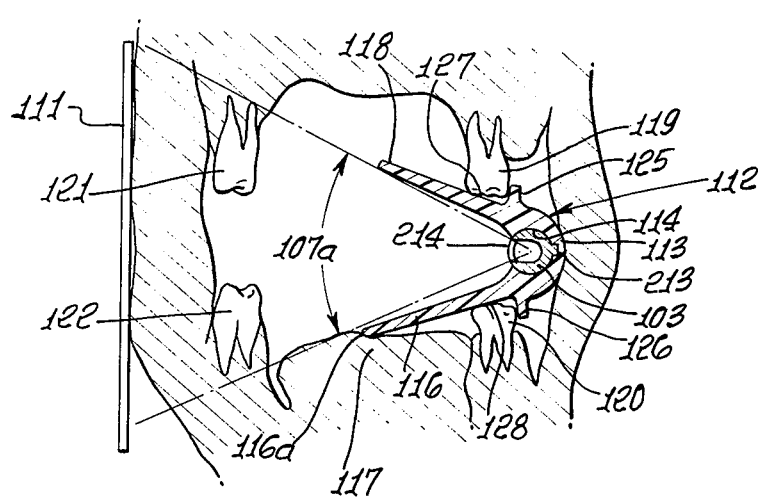
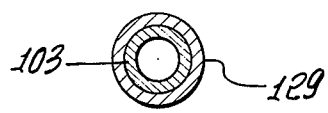

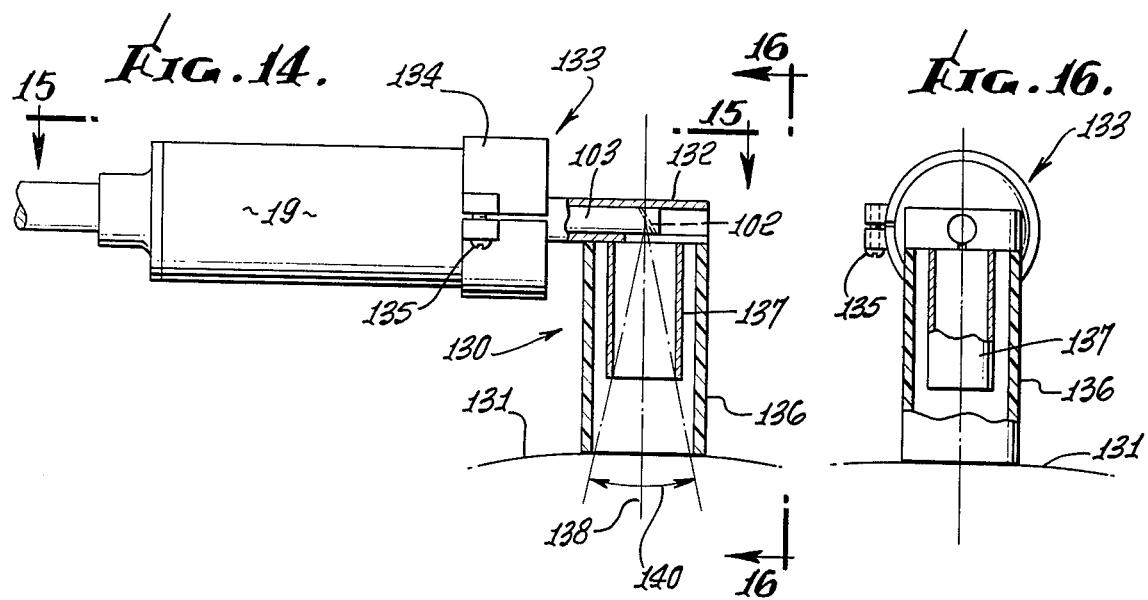
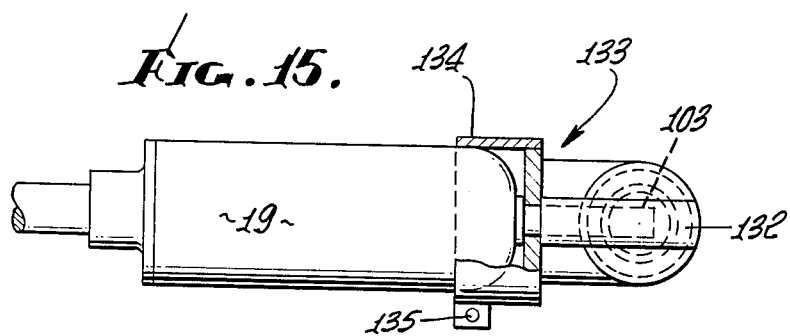
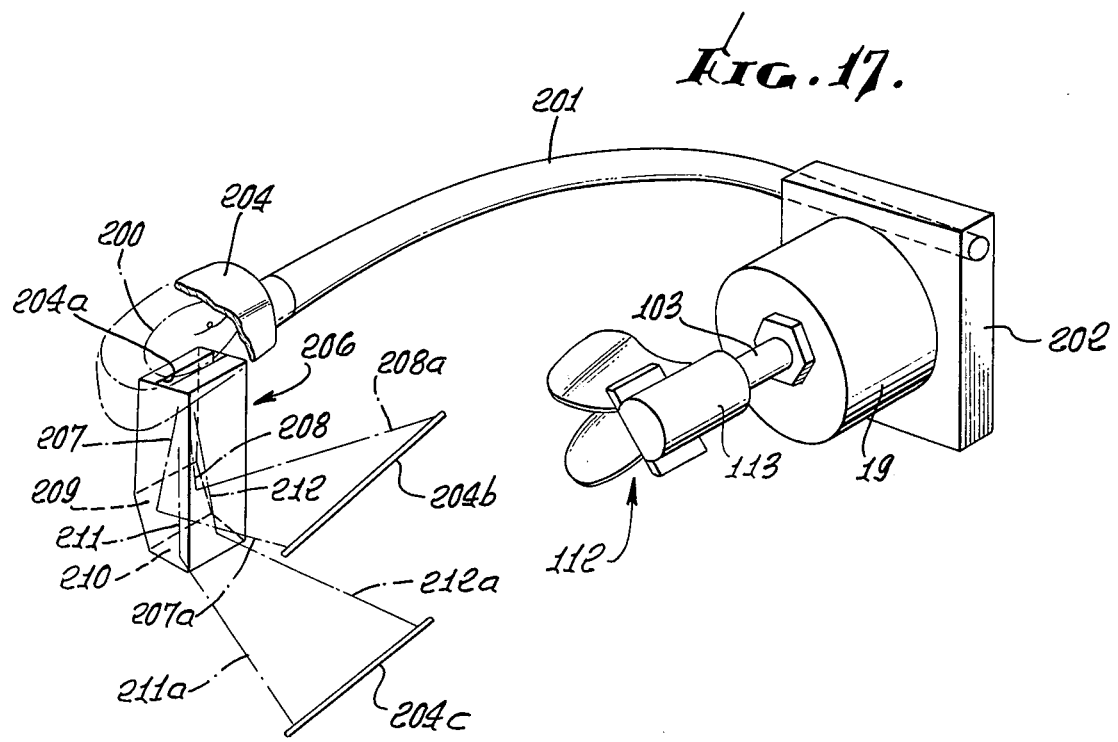

DENTAL AND MEDICAL X-RAY APPARATUS

BACKGROUND OF THE INVENTION

This application is a continuation-in-part of my earlier application Ser. No. 672,608, filed Apr. 1, 1976 and entitled "Dental and Medical X-ray Apparatus", abandoned.

This invention relates generally to X-ray apparatus and techniques; more particularly, it concerns method equipment enabling rapid X-ray examination of teeth, with substantially reduced exposure to radiation.

Present systems of X-ray examination of human teeth require twelve to fourteen exposures, accompanied by objectionably excessive amounts of side radiation to sensitive areas of the brain, cortex, sinus, throat, optic and auditory nerve centers. Recently, a technique has been proposed according to which an X-ray target is introduced into the mouth, and radiation is directed from the target back through the teeth to film supported outside the mouth, thereby to produce a so-called high resolution, panoramic radiograph. One problem encountered with that type equipment concerns the tendency to produce gagging of the patient, due to the necessity of locating the target sufficiently close to the throat that back teeth will be exposed to produced X-rays. Another problem has to do with the requirement that the upper and lower teeth be alternately exposed to radiation, which in turn requires that the shield associated with the target be re-arranged. This means that the target is removed from the oral cavity after the first exposure (as for example irradiation of the upper teeth, after which the target is re-introduced to enable the second exposure (of the lower teeth) which increases the risk of gagging and otherwise discomforts the patient.

SUMMARY OF THE INVENTION

It is a major object of the invention to provide improvements in technique and apparatus which will overcome the above objects and disadvantages. Another object is to provide target and shield configurations within the oral cavity whereby gagging will be eliminated, and all of the front and rear teeth will be irradiated, while flat upper and lower portions of the mouth and sensitive areas of the head will not be directly exposed to X-rays.

Basically, the invention is embodied in apparatus that includes:

(a) X-ray tube means providing an electron beam,
(b) a beam target carried by said means and located axially rearwardly thereof to be received rearwardly into a patient's mouth,
(c) the target angled relative to said axis to produce a radiation pattern that extends forwardly of the target and also rearwardly and sidewardly of the target, and
(d) a shield extending forwardly above and below the target and also rearwardly thereof.

As will be seen, the shield typically projects forwardly both above and below the target to block radiation from passing to patient's head zones above the upper teeth and below the lower teeth; the shield may typically provide lateral openings to pass X-rays toward the back upper and lower teeth; the target may typically be angled rearwardly and sidewardly at one or both sides of the equipment axis so that radiation may pass through one or both of the shield side openings to provide access to the back teeth as well as front teeth; and the radiation pattern produced by the target may be transversely shifted, as for example by sideward deflection of the beam to strike different portions of the target, or by physical rotation of the target, so that the target need not be removed from the mouth between exposure.

A further important object of the invention is to provide X-ray shielding and tongue suppressor means carried to be received into the patient's mouth, and characterized in that when the target is located at one side of the mouth to direct an X-ray beam toward teeth at the opposite side of the mouth the shield will protect portions of the head from the X-ray beam and the patient's tongue will be suppressed relative to the X-ray beam. As will appear, the apparatus may include a tubular carrier for the target projecting rearwardly of the X-ray tube itself, and the shielding and tongue suppressor means may advantageously comprise a component having a base defining an opening removably receiving the tubular carrier; further, that component may have arms which project sidewardly of the base with V-shaped configuration, the lower arm extending sufficiently downwardly and sidewardly as to suppress the patient's tongue when the base is received between the patient's upper and lower molars. In this regard, the referenced component may consist of plastic material containing X-ray shielding substance, as for example barium; and it may carry upper and lower projections to fit adjacent the outer sides of the patient's upper and lower molars for positioning purposes, and so that the molars may clench the component to position it for tongue suppression and shielding orientation relative to the mouth and head of the patient; also a longer source to film distance is enabled. Finally, means is provided to visually delineate on the patient's head a zone subjected to irradiation so that film may be accurately located.

These and other objects and advantages of the invention, as well as the details of illustrative embodiments, will be more fully understood from the following description and drawings in which:

DRAWING DESCRIPTION

FIGS. 4 and 5 are top plan views of gun and target relationships, in schematic form;

FIG. 6 is an enlarged frontal view of the target and shield;

FIG. 7 is a view like FIG. 4 in FIG. 5, but showing an alternative target; and FIG. 8 shows another target;

FIG. 7a is a section taken on lines 7a—7a of FIG. 7;

FIG. 9 is a view like FIG. 5, showing modified apparatus wherein the target is located at one side of the patient's mouth;

FIG. 10 is a perspective view of an X-ray shield and tube positioning tongue suppressor attachment;

FIG. 11 is a vertical section taken through a patient's mouth showing use of the FIG. 10 attachment in conjunction with an X-ray tube, target and carrier as for example is shown in FIG. 9;

FIG. 12 is a plan view of a carrier for an X-ray producing target, and showing a filter on the carrier;

FIG. 13 is a cross-section taken on lines 13—13 of FIG. 12;

FIG. 14 is a side elevation showing an attachment for the FIG. 9 apparatus, enabling its use externally of the patient's mouth;

FIG. 15 is a plan view taken on lines 15—15 of FIG. 14;

FIG. 16 is an elevation taken on lines 16—16 of FIG. 14; and

FIG. 17 is a perspective view of means to delineate a head zone to be irradiated.

DETAILED DESCRIPTION

Figure 1:
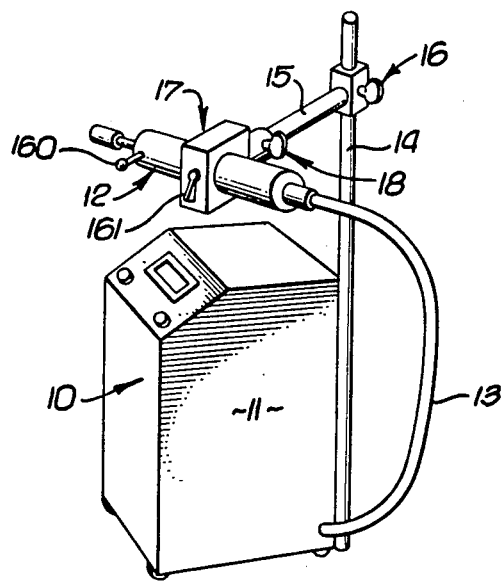
FIG. 1 is a perspective showing of high voltage generator equipment and X-ray tube mobile or floor mount associated with the invention.

Referring first to FIG. 1, X-ray apparatus 10 includes a high voltage generator console 11 to which X-ray tube 12 is electrically connected, as via cable 13. A suitable adjustable support for the tube 12 includes upright post 14 carried by the console; an arm 15 adjustably attached at 16 to the post to rotate about a vertical axis; and a mount 17 for the tube apparatus and adjustably attached at 18 to the arm 15 to rotate or swivel about a horizontal axis.

Figure 2:
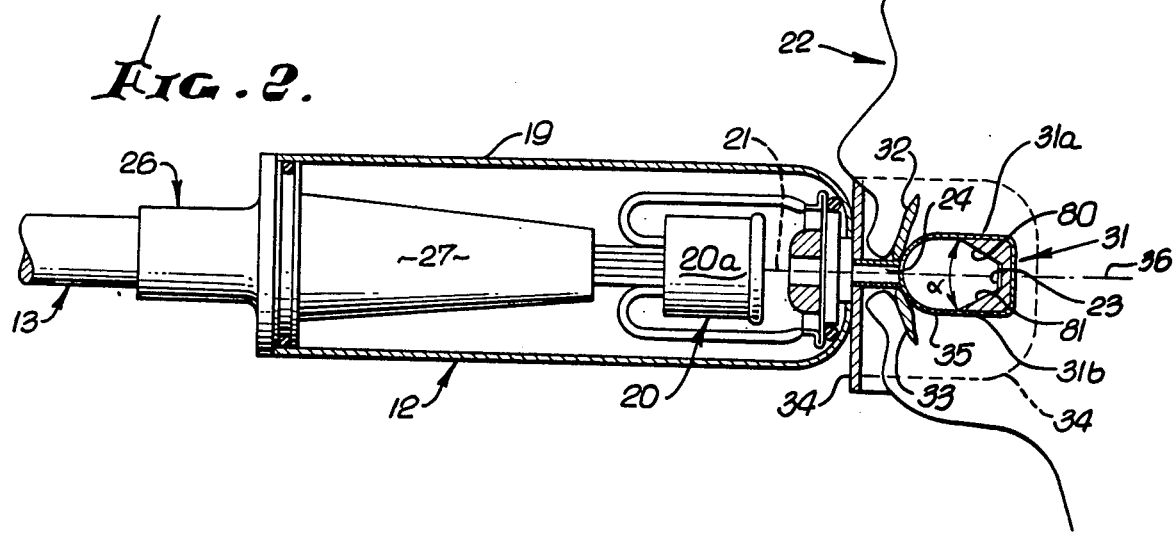
FIG. 2 is a cross sectional view of gun and target apparatus embodying the invention.

Extending the description to FIG. 2, the tube means 12 includes a housing 19 containing the micro-focus X-ray tube 20 which produces an electron beam 21. A beam target 23 is carried by the tube means and is located axially rearwardly thereof (relative to the patient's head 22) to be inserted or received relatively rearwardly into the patient's mouth. The forward and rearward axis appears at 36. In the example shown, the target 23 is carried by the rearward end portion of a rearwardly axially elongated tubular element 24 projecting into the patient's mouth. The cable 13 is attached to the housing at 26, and passes through an insulator 27 to the gun 20a. The inner conductor of the cable is at high potential while the outer cable sheath is at ground potential and is solidly connected to the tube housing. The tube anode is also at ground potential and only the electron gun 20a is at high potential, insulated by gas or oil inside the tube housing. This provides the necessary electrically shock-proof mounting for intraoral radiography.

Figure 3:
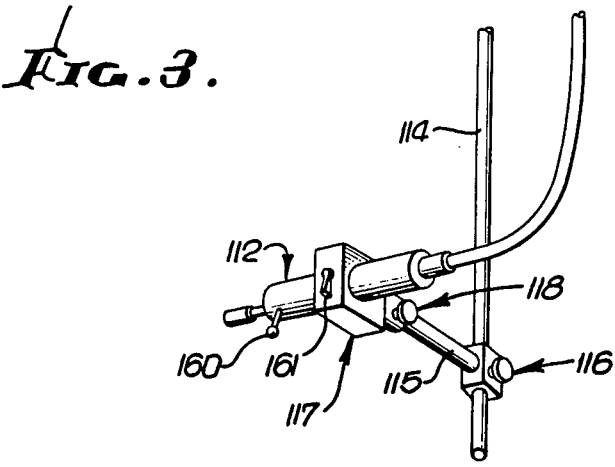
FIG. 3 is a perspective showing of an alternative X-ray tube ceiling or wall mounting.

An alternative ceiling mount for the tube 112 in FIG. 3 includes an upright post 114 affixed to or carried by the ceiling of a room. Elements 115-118 correspond to elements 15-18 in FIG. 1.

The target 23 may consist of tungsten embedded in a copper shield 31, the latter having upper and lower rearwardly tapering surfaces 80 and 81 which define an angle α there-between. That angle subtends a zone which encompasses the patient's upper and lower teeth (including root areas) indicated at 32 and 33, but not including the brain or sinus area, the latter as well as the throat being protected from radiation impingement. In this regard, an X-ray film holder 34 is carried by the apparatus 12 to extend at the front of the patient's mouth, and to overlap his cheeks at opposite sides of the mouth. The film holder is also substantially subtended by the angle α. Alternatively, the film may be held in place against the patient's face as by an elastic strap wrapped around his head, or the strap may incorporate VELCRO holding means. The target and shield are carried by the anode envelope 35 which is in turn carried by the tubular element 24. The anode envelope material is a low X-ray absorbtion material such as beryllium, titanium or aluminum, and forms the window for radiation emission.

Extending the description to FIG. 4, the tube anode 37 is shown axially rearwardly of the gun 20a. The target 23, located axially rearwardly of the anode, has surfaces 23a and 23b angled rearwardly and transversely (i.e. sidewardly) relative to the axis 36. Surfaces 23a and 23b are transversely symmetrical relative to axis 36, and taper axially forwardly, as shown, at angles β relative to an upright plane 39 normal to axis 36; angle β may for example be about 20°.

In accordance with an important aspect of the invention, means is provided to effect transverse shifting of the radiation pattern produced in respone to beam incidence on the target. Such means may comprise a magnet supported to be shifted transversely to deflect the beam transversely relative to the target; for example, FIG. 4 shows the magnet 40 suitably supported at 41 by the tube at the right side of the axis 36, and rearwardly of the anode 37, the magnet acting to deflect the beam 21 transversely rightwardly so that it impinges on surface 23a. As a result, X-rays are produced to travel forwardly through the upper and lower teeth at the right side of the patient's mouth and to the film in holder 34, such teeth indicated at 44. Actually, radiation may extend transversely over the 180° angle indicated, and defined by the plane of surface 23a, and the shield does not interrupt such sideward radiation. See in this regard the shield openings 45 at opposite sides of the target, in FIG. 6. Accordingly, the shield has sections 31a and 31b above and below the target.

Upon completion of exposure of the right side teeth 44 to X-radiation, the magnet 40 is transversely shifted to the left side of axis 36, i.e. to a position as for example appears in FIG. 5. In that position, suitably supported at 41a by the tube, the magnet acts to deflect the beam 21 transversely leftwardly, so that it impinges on target left surface 23b. As a result, X-rays are produced to travel forwardly through the patient's upper and lower teeth at the left side of the mouth, and to the film in the holder 34, such teeth indicated at 44a. Here again, radiation may extend transversely over the 180° angle indicated and defined by the plane of surface 23b. The shield does not interrupt such sideward radiation, but does limit radiation in upper and lower directions, to remain within the angle α previously described.

Holders 41 and 41a may suitably releasably retain the magnet, as by detents. If desired, the magnet 40 may be rotatably carried to swing about axis 36 between the positions seen in FIGS. 4 and 5.

FIG. 7 shows an alternative means to effect transverse shifting of the X-ray pattern with a fixed target, seen in FIG. 8. In this view, the tube 12 and supported target 170 are rotatable about axis 136 between the solid line and broken line target surface positions shown at 50 and 50a. For example, in FIG. 1 the mount 17 may incorporate means to rotatably support the tube 12 to rotate about axis 136. A sidewardly projecting handle to rotate the tube 180° outside the mouth appears at 160. A tube position locking toggle appears at 161. In target position 50, the operation corresponds to that described in FIG. 4; whereas in target position 50a, the operation corresponds to that described in connection with FIG. 5. Envelope 135 and support element 124 correspond to items 35 and 24 in FIG. 2.

FIG. 8 shows the modified tungsten target 70 supported by shield 71, the latter projecting forwardly at 71a sidewardly of the target to block X-ray sideward travel and confine same to the region 72. The latter is related to teeth 144 at one side of the mouth, as shown.

Portions of the copper shield 71 not shown extend above and below the target and forwardly as in FIG. 6, so that a side opening is formed at only one side of the target. Target 70 and shield 71 rotate with the tube, as explained above.

Finally, it should be pointed out that since the X-ray intensity necessary for the required film density is porportional to the square of the focus-to-film distance, the radiation output of the X-ray source at 5cm need be only 1/25 or 4% of that required at 25cm with the conventional extraoral X-ray tube distance.

The wide-angle radiation pattern of the present tube can expose a panoramic view of half the mouth including upper and lower teeth in one exposure, so that only two X-ray pictures are necessary instead of 12 with conventional extraoral tubes. When this correction 1/6 is included in the 4% noted above, the total reduction in radiation amounts to only .66% of that required with conventional dental radiaography for the same visual information. This is a very significant reduction in radiation dosage which is less than 1% of the present radiation level for whole-mouth dental radiography.

Referring to FIG. 9, the modified apparatus 100 includes an X-ray tube means 101, and a target 102 spaced from the tube to be received rearwardly into a patient's mouth. A tubular carrier element 103 for the target is attached to the tube means as at 104 and projects rearwardly. The target may be supported by a shield 105 similar to shield 71 described above. It is carried by the carrier tube 103 and projects forwardly at 105a sidewardly of the target to block X-ray sideward travel in the direction 106 and confine X-ray travel to the region designated at 107. The latter is related to teeth 108 at one side of the mouth, as shown. Portions of the shield extend above and below the target (as in FIG. 7a) and forwardly of the target as at 105b, so that a side opening is formed at only one side of the target. The target and shield rotates with the carrier probe or tube 103, and a window 109 is formed in the latter to pass X-rays. With the 30° target oriented as shown, and between upper and lower molars at one side of the mouth, the sidewardly directed wide angle X-ray beam at 107 traverses all the upper and lower teeth 110 at the opposite side of the mouth, a film 111 being located outside or inside the mouth and proximate teeth 110 for exposure to the X-radiation and recordation of tooth and gum images. Accordingly, only two exposures are needed to record images of all teeth, one exposure as illustrated, and an opposite side (mirror image) exposure with the target located between the molars at the opposite side of the mouth and directing X-rays rightwardly.

Referring to FIGS. 10 and 11, the elements 100-105 and 109 remain as in FIG. 9; however, additional and very important structure is provided, namely, X-ray shielding and tongue suppressor means carried by the apparatus to be received into the patient's mouth and characterized in that when the target is located at one side of the mouth to direct an X-ray beam toward teeth at the opposite side of the mouth the shield will protect portions of the mouth from the X-ray beam and the patient's tongue will be suppressed relative to the X-ray beam. While such apparatus may take various forms, that form as illustrated by component 112 in FIGS. 10 and 11 is of unusual advantage. It includes a base 113 which is rearwardly lengthwise elongated and forms an elongated opening or semi-circular bore 114 sized to snugly receive the tube 103, i.e. with frictional or other (such as tongue and groove at 213) interfit resisting relative rotation of the component 112 and tube 103. Preferably, the component 112 has removable attachment to the tube 103, for ready replacement by another component for use with a different patient. Thus, component 112 may be dispensible, and provides a new, sterile hygienic cover for the tube 103 for each use. Tube 103 may consist of copper or Monel, and have a titanium window 214 to pass radiation.

The component 112 also typically includes arms projecting sidewardly from the C-shaped base 113 with V-shaped relative configuration, the radiation passing between the arms. As illustrated, the lower arm 116 extends downwardly and sidewardly sufficiently to extend centrally over the patient's tongue 117 to forcibly supress same out of the main path of the radiation beam, the vertical path of which may sweeps an arc such as at 107a in FIG. 11. Note the edge 116a of arm 116 over the center of the tongue, with base 113 clenched between the patient's upper and lower molars 119 and 120 at one side of the mouth (the right side, as also related to FIG. 9). The upper arm 118 typically extends upwardly and sidewardly toward the root area of the upper molars 121 at the opposite side of the mouth, and in this regard, arm 116 typically extends toward the root area of molars 122. The two arms also function as shields to prevent X-ray travel outside the path or arc 107a, i.e. protecting the palate and below tongue areas of the head, containing sensitive gland, sinus and brain zones. The X-ray paths 107 and 107a may include the temporo-mandibular joint.

The component 112 may advantageously consist of plastic material (such as polyethylene) containing X-ray shielding material, as for example barium particles dispersed throughout the plastic in as-molded or formed condition. Other shield substances and component compositions may be utilized.

In the mode of use as illustrated in FIGS. 9 and 11, with a substantially longer source-to-image distance than is characteristic of FIG. 4 use, the magnification, distortion and geometric unsharpness are all reduced to improve the overall resolution of the X-ray beam.

FIG. 11 also illustrates the provision of upper and lower integral projections or tabs 125 and 126 on the component 112, to engage the outsides of the posterior molars as shown. They aid in positioning the component relative to the molars when the patient bites down onto the outer surfaces 127 and 128 of the component. Pockets are formed between the lengthwise extending tabs 125 and 126 an arms 116 and 118, to receive and locate the molars, during bite-down, firmly locating the arms 116 and 118.

FIGS. 12 and 13 show the provision of an additional X-ray filter 129 extending over the tube 103. Tubular filter 129 may consist of aluminum or other shielding material. The filter may form a window to register with window 109.

FIGS. 14-16 illustrate the use of an extra-oral source adapter removably carried by the tube 103. The adapter structure 130 typically projects sidewardly of the carrier tube 103 and target 102, and is located to pass an X-ray beam sidewardly from the target toward a patient's anatomy, and exteriorly thereof. For example the structure may be placed against the cheek area 131 adjacent the teeth, the X-ray film then being located inside the mouth in a conventional manner. The structure 130 may include a support cylinder 132 removably slipped onto or over the tube 103, and suitably secured to the X-ray tube housing, as at 133. The latter may include a bracket 134 which encompasses the housing 19 and may be clamped thereto as by tightening screw 135.

The structure 130 includes beam collimator means defined by plastic cylinder 136 and internal metallic tubular shield 137. These elements extend generally coaxially with respect to the axis 138 of the X-ray beam embraced by arc 140. Element 136 projects further from the cylinder 132 than element 137, and both tend to limit the beam to a narrow cone circumscribing the rectangular periapical X-ray film used in conventional extra-oral radiography.

Among the advantages of the above apparatus are the following:

1. Increased magnification of the tooth area facilitates diagnosis; for example, detection of pulp in the root area is made easier, and the results of grinding of teeth show up more clearly. Thus, the dentist can more accurately inform the patient of grinding and the deleterious results of same including possible injury to the jaw hinge joint. Splintering of teeth is also more easily detectable, and sinus areas can be X-rayed to show up more clearly.

2. The depression of the tongue prevents obscuration of the film.

3. The aluminum filter on the tubular carrier tends to even out the beam intensity over the film area, producing a better picture.

4. The side-to-side interior X-ray technique enabled by the invention facilitates rapid taking of full mouth X-rays, using only two exposures, which in turn facilitates accurate charting of teeth by the dentist. Also, the patient can be shown the full X-ray picture, and can easily see what dental work needs to be done, so that communication between dentist and patient is improved.

5. The invention used for panoramic radiographs removes need for conventional bite-wings and their holders inserted into the mouth, obviating discomfort and injury that can result from these items.

6. The probe itself (target and carrier) can be used in emergencies such as accidents wherein patients undergo severe facial injury, so as to secure pictures of the extent of that injury. Also, information highly useful for plastic surgery can be easily obtained.

7. Irradiation of sensitive areas of the brain, optic nerve, thalmus and thyroid glands is avoided.

8. Full X-ray data, obtainable through use of the invention, is easily obtained for use as best evidence in legal proceedings.

Finally, FIG. 17 illustrates the provision of support operatively connected to the above described X-ray tube means, together with other means carried by the support at a location to project toward the patient's head an image delineating an area within the main path of the X-ray beam. As illustrated, such other means typically includes a light source 200 carried by the support arm 201, the latter extending from a mount 202 attached to the X-ray tube housing 19. The light source 200 may be suitably shielded at 204.

Light refracting structure is located in the path of light transmitted from the source 200, such structure advantageously taking the form of a double prism 206 attached to the shield 204, for example, and extending in openly spaced confronting relation to the component 112. Light projected downwardly via iris 204a and in the prism, as ray 207 and 208 is reflected by prism face 209 as rays 207a and 208a, and an upper image 204b of the iris 204a in the shield may be formed between the rays 207a and 208a as for example on a patient's face. Similarly, light projected downwardly via the iris as rays 211 and 212 is reflected by prism face 210 as rays 211a and 212a and a lower image 204c of the iris may be formed between the rays 211a and 212a as on a patient's face. Images 204b and 204c delineate the upper and lower limits of a facial area in the main path 107 of the X-rays from the target. Accordingly, the technician will know precisely where to locate the X-ray film adjacent the patient's face.

I claim:

1. In dental X-ray apparatus,
   (a) X-ray tube means for providing an electron beam,
   (b) a target for said beam carried by said means and spaced therefrom to be received rearwardly into a patient's mouth,
   (c) a carrier element projecting rearwardly of the tube means and carrying said target, said carrier element and target being interconnected,
   (d) and X-ray shielding and tongue suppressing means carried by said carrier element to be received into the patient's mouth, and characterized in that when the target is located at one side of the mouth to direct an X-ray beam toward teeth at the opposite side of the mouth the shield will protect portions of the head from the X-ray beam and the patient's tongue will be suppressed relative to the X-ray beam, said means projecting sidewardly of and relatively away from the carrier element.

2. The apparatus of claim 1 wherein said shielding and tongue suppressor means is carried by said carrier element to be removable therefrom.

3. The apparatus of claim 1 wherein said carrier element is tubular, and said shielding and tongue suppressor means defines a generally cylindrically shaped opening removably receiving said tubular element.

4. The apparatus of claim 3 wherein said shielding and tongue suppressor means comprises a component having a base defining said opening which projects lengthwise rearwardly, and arms projecting sidewardly from the base with V-shaped relative configuration, the lower arm extending sufficiently sidewardly and downwardly relative to the base as to suppress the patient's tongue when the base is received between the patient's upper and lower molars.

5. The apparatus of claim 4 wherein said component consists of plastic material containing X-radiation shielding substance.

6. The apparatus of claim 1 wherein said shielding and tongue suppressor means comprises a component having a base which extends generally lengthwise rearwardly, and upper and lower arms projecting sidewardly from the base to define a wedge-shaped slot therebetween to pass X-rays, the lower arm extending sufficiently sidewardly and downwardly relative to the base as to suppress the patient's tongue when the base is received between the patient's upper and lower molars.

7. The apparatus of claim 6 wherein said component consists of plastic material containing X-ray shielding substance.

8. The apparatus of claim 7 wherein said substance consists of barium.

9. The apparatus of claim 6 wherein said base is generally C-shaped, and said component includes upper and lower projections to engage the outer sides of said molars.

10. The apparatus of claim 4 wherein said tubular carrier element forms an X-ray window opening toward the region between said arms, the V-shape of said arms forming an acute angle.

11. The apparatus of claim 2 wherein said carrier element is tubular, and including an X-ray filter sleeve received on the tubular carrier, the sleeve consisting of metal.

12. In dental X-ray apparatus,
 (a) X-ray tube means for providing an electron beam,
 (b) a target for said beam spaced from said means to be received rearwardly into a patient's mouth,
 (c) a carrier element projecting longitudinally rearwardly of the tube means and carrying said target, the carrier element and target being interconnected, and
 (d) tubular structure removably carried by said carrier element and located to pass an X-ray beam sidewardly from the target toward a patient's anatomy and exteriorly thereof, said tubular structure having a laterally projecting axis and said structure extending about said axis and projecting laterally outside of and away from said carrier element and target.

13. The apparatus of claim 12 wherein said structure includes an X-ray beam shielding tube, and a cylindrical collimator element surrounding the tube.

14. In dental X-ray technique, the steps that include
 (a) providing an X-ray source, and tongue suppressor and X-ray shield means, said means and source being interconnected,
 (b) locating said source and said means between the upper and lower molars of the patient which grip the unit at one side of the patient's mouth, thereby to locate the tongue suppressor in tongue suppressing position, and
 (c) using said source to produce X-rays in the patient's mouth and directed through teeth at the opposite side of the mouth, while said means operates to shield a portion of the patient's head from said X-rays, and
 (d) receiving said X-rays on film proximate said opposite side of the patient's mouth.

15. The method of claim 14 which includes the step of providing a tubular carrier for said target, and removably mounting said means on said carrier for insertion into the patient's mouth.

16. Apparatus as defined in claim 1 including a support operatively connected to said X-ray tube means, and other means carried by said support at a location to project toward the patient's head an image delineating an area within the main path of the X-ray beam.

17. The apparatus as defined in claim 16 wherein said other means includes a light source and light refracting structure in the path of light transmitted from said source, said structure openly spaced from said X-ray shielding and tongue suppressor means.

18. In apparatus for intra-oral source dental radiography,
 (a) X-ray tube means providing an electron beam,
 (b) a flat target for said beam carried by said means and located axially rearwardly thereof to be received rearwardly into a patient's mouth,
 (c) the target angled relative to said axis to produce a radiation pattern that extends forwardly of the target and also rearwardly and sidewardly of the target, and
 (d) a shield adjacent the target rearwardly thereof and extending forwardly above and below the target, and
 (e) means carried by the shield and projecting sidewardly away from the shield to define a sidewardly projecting and confined passage to receive and pass said radiation pattern,
 (f) said last named means, shield and target being interconnected.

19. For use in combination with a hollow probe containing an electron beam target adapted to produce an X-ray beam passing through a window at the side of the probe, the target and probe being interconnected, the probe adapted for intra and extra oral use,
 (a) intra-oral means removably attachable to the probe to extend sidewardly therefrom for providing an X-ray beam shield and tongue suppressing means,
 (b) said means defining a diverging passage extending away from the probe.

20. For use in combination with a unit including a hollow longitudinally elongated probe containing an electron beam target adapted to produce an X-ray beam passing through a window at the side of the probe, the probe adapted for intra and extra oral use, the probe and target being interconnected,
 (a) extra-oral means removably attachable to the unit to extent laterally sidewardly from the probe for providing a sidewardly extending tubular collimator to pass an X-ray beam sidewardly toward a patient's anatomy and exteriorly thereof.
 (b) said means having a tubular portion sized to fit over said probe, said portion defining a longitudinally extending probe receiving opening.

21. For use in combination with a unit including a hollow probe containing an electron beam target adapted to produce an X-ray beam passing through a window at the side of the probe, the target and probe being interconnected, the probe adapted for intra and extra oral use,
 (a) intra-oral means removably attachable to the probe to extend sidewardly therefrom for providing an X-ray beam shield and tongue suppressing means, and
 (b) extra-oral means removably attachable to the unit to extend sidewardly from the probe for providing a sidewardly extending tubular collimator to pass an X-ray beam sidewardly toward a patient's anatomy and exteriorly thereof.

* * * * *